(12) United States Patent
Jesse

(10) Patent No.: US 6,955,259 B1
(45) Date of Patent: Oct. 18, 2005

(54) SYRINGE STORAGE DEVICE

(76) Inventor: Robert A. Jesse, P.O. Box 584, Pine River, MN (US) 56474

( * ) Notice: Subject to any disclaimer, the term of this patent is extended or adjusted under 35 U.S.C. 154(b) by 116 days.

(21) Appl. No.: 10/671,961

(22) Filed: Sep. 26, 2003

(51) Int. Cl.$^7$ .............................................. B65D 83/10
(52) U.S. Cl. ...................... 206/366; 206/370; 206/485; 211/60.1; 211/85.13
(58) Field of Search ................................ 206/364–366, 206/370, 443, 485; 211/60.1, 69, 69.1, 70.6, 211/85.13

(56) References Cited

U.S. PATENT DOCUMENTS

| | | | | |
|---|---|---|---|---|
| 4,606,455 A | * | 8/1986 | Grikis et al. ................ 206/485 |
| 4,871,074 A | * | 10/1989 | Bryson et al. ............. 211/70.6 |
| 4,929,427 A | * | 5/1990 | Guala ......................... 206/366 |
| 5,133,454 A | * | 7/1992 | Hammer ..................... 206/366 |
| 5,279,578 A | * | 1/1994 | Cooke ......................... 206/365 |
| 5,311,985 A | * | 5/1994 | Suida .......................... 206/366 |
| 5,678,700 A | * | 10/1997 | Crosson, Jr. ............... 211/60.1 |
| 6,257,408 B1 | * | 7/2001 | Odierno ...................... 206/366 |

\* cited by examiner

Primary Examiner—Luan K. Bui

(57) ABSTRACT

Syringe storage devices safely secure a syringe during ambulance treatment and transport of patients. A base has a plurality of mounting holes in its opposing sides and a plurality of adhesive tabs on its back to facilitate its attachment to an interior wall or cabinet of an ambulance. The front of the base has a plurality of clips and a shelf attached to it. Needle holes are present in the middle of the shelf beneath each clip. The needle holes and clips are adapted to receive and removably secure the needle cover and syringe body of a syringe. A portion of the front of the base beneath the shelf comprises a dry erase board where a user can use a dry erase pen to create a syringe label identifying the contents of the syringe removably stored above it.

2 Claims, 4 Drawing Sheets

SYRINGE STORAGE DEVICE

BACKGROUND OF THE INVENTION

1. Field of the Invention

The present invention relates to a syringe storage device for use in connection with medicine. The syringe storage device has particular utility in connection with safely securing a syringe during ambulance treatment and transport of patients.

2. Description of the Prior Art

Syringe storage devices are desirable for safely securing a syringe during ambulance treatment and transport of patients. Syringes are frequently used in a variety of medical environments. However, syringes must be handled carefully to avoid contamination or accidental needle sticks. In the fast-paced environment of emergency medicine, such as within ambulances, syringes are currently taped to a wall or placed on a jump seat, leaving them at significant risk of falling, becoming lost or contaminated, or accidentally sticking someone. Syringe storage devices provide a safe and effective means for storing syringes when they are not in use on a patient.

The use of syringe dosage tracking devices with cooling feature is known in the prior art. For example, U.S. Pat. No. 5,850,917 to Denton et al. discloses a syringe dosage tracking device with cooling feature. However, the Denton et al. '917 patent does not have a clip, and has further drawbacks of not attaching to an interior wall or cabinet in an ambulance.

U.S. Pat. No. 6,267,256 to Thilly discloses storage devices that store syringes. However, the Thilly '256 patent does not have a clip, and additionally does not attach to an interior wall or cabinet in an ambulance.

Similarly, U.S. Pat. No. 4,383,615 to Aquino discloses a syringe tray that receives the needle sheaths of syringes. However, the Aquino '615 patent does not have a clip, and cannot attach to an interior wall or cabinet in an ambulance.

In addition, U.S. Pat. No. 5,823,363 to Cassel discloses a medical syringe holding/transport apparatus that receives and holds a plurality of syringes of differing size. However, the Cassel '363 patent does not have a clip, and also does not attach to an interior wall or cabinet in an ambulance.

Furthermore, U.S. Pat. No. Des. 424,692 to Monaghan et al. discloses a syringe holder that holds syringes. However, the Monaghan et al. '692 patent does not have a needle hole, and further lacks a shelf.

Lastly, U.S. Pat. No. 2,313,905 to Wallin discloses a hypodermic needle rack that supports hypodermic needles in a convenient and accessible position. However, the Wallin '905 patent does not have a clip, and has the additional deficiency of not attaching to an interior wall or cabinet in an ambulance.

While the above-described devices fulfill their respective, particular objectives and requirements, the aforementioned patents do not describe a syringe storage device that allows safely securing a syringe during ambulance treatment and transport of patients. The Denton et al. '917 patent, the Thilly '256 patent, the Aquino '615 patent, the Cassel '363 patent, and the Wallin '905 patent make no provision for a clip. The Denton et al. '917 patent, the Thilly '256 patent, the Aquino '615 patent, the Cassel '363 patent, and the Wallin '905 patent cannot be attached to an interior wall or cabinet in an ambulance. The Monaghan et al. '692 patent lacks a needle hole and a shelf.

Therefore, a need exists for a new and improved syringe storage device that can be used for safely securing a syringe during ambulance treatment and transport of patients. In this regard, the present invention substantially fulfills this need. In this respect, the syringe storage device according to the present invention substantially departs from the conventional concepts and designs of the prior art, and in doing so provides an apparatus primarily developed for the purpose of safely securing a syringe during ambulance treatment and transport of patients.

SUMMARY OF THE INVENTION

In view of the foregoing disadvantages inherent in the known types of syringe dosage tracking devices with cooling feature now present in the prior art, the present invention provides an improved syringe storage device, and overcomes the above-mentioned disadvantages and drawbacks of the prior art. As such, the general purpose of the present invention, which will be described subsequently in greater detail, is to provide a new and improved syringe storage device which has all the advantages of the prior art mentioned heretofore and many novel features that result in a syringe storage device which is not anticipated, rendered obvious, suggested, or even implied by the prior art, either alone or in any combination thereof.

To attain this, the present invention essentially comprises a base with a clip attached to its front and one side of a shelf attached to one end of its front. The middle of the shelf has a needle hole in it.

There has thus been outlined, rather broadly, the more important features of the invention in order that the detailed description thereof that follows may be better understood and in order that the present contribution to the art may be better appreciated.

The invention may also include the base being generally rectangular in shape. The syringe clip may comprise a left clip member attached to the front of the base and a right clip member attached to the front of the base. The left clip member and the right clip member may be arctuate in shape. The left clip member and the right clip member may be mirror images of one another. There may be a plurality of mounting holes in the opposing sides of the base. At least a portion of the front of the base may comprise a dry erase board. The base and the syringe clip may be made of plastic, steel, aluminum, titanium, wood, or carbon fiber composite. There may be adhesive tab with its front attached to the back of the base with a peel off backing removably attached to its back. The syringe clip may be adapted to fit a syringe body. The needle hole may be adapted to fit a needle cover. There may be a plurality of syringe clips attached to the front of the base. There may be a plurality of needle holes in the middle of the shelf. At least a portion of the front of the base may be written on by a dry erase pen or a water-soluble pen. The base may be generally square in shape with rounded corners. There may be a plurality of left clip members and right clip members attached to the front of the base. A plurality of the left clip members, right clip members, and needle holes may be adapted to hold a 1 cc syringe. There may be a plurality of adhesive tabs with their fronts attached to the back of the base atop the mounting holes and a plurality of peel off backings removably attached to the back of the adhesive tabs. There may be a plurality of mounting holes in the middle of the adhesive tabs. There are, of course, additional features of the invention that will be described hereinafter and which will form the subject matter of the claims attached.

Numerous objects, features, and advantages of the present invention will be readily apparent to those of ordinary skill in the art upon a reading of the following detailed description of presently current, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved syringe storage device that has all of the advantages of the prior art syringe dosage tracking devices with cooling feature and none of the disadvantages.

It is another object of the present invention to provide a new and improved syringe storage device that may be easily and efficiently manufactured and marketed.

An even further object of the present invention is to provide a new and improved syringe storage device that has a low cost of manufacture with regard to both materials and labor, and which accordingly is then susceptible of low prices of sale to the consuming public, thereby making such syringe storage device economically available to the buying public.

Still another object of the present invention is to provide a new syringe storage device that provides in the apparatuses and methods of the prior art some of the advantages thereof, while simultaneously overcoming some of the disadvantages normally associated therewith.

Even still another object of the present invention is to provide a syringe storage device for safely securing a syringe during ambulance treatment and transport of patients. This allows a user to removably secure a syringe when it is not in use.

Still yet another object of the present invention is to provide a syringe storage device for safely securing a syringe during ambulance treatment and transport of patients. This makes it possible to attach the syringe storage device to an interior wall or cabinet in ambulance.

An additional object of the present invention is to provide a syringe storage device for safely securing a syringe during ambulance treatment and transport of patients. This prevents a syringe from becoming lost or contaminated.

A further object of the present invention is to provide a syringe storage device for safely securing a syringe during ambulance treatment and transport of patients. This prevents a person from accidentally being stuck with a syringe.

A still further object of the present invention is to provide a syringe storage device for safely securing a syringe during ambulance treatment and transport of patients. This allows the user to label the syringe storage device with the types of substances contained in the stored syringes.

Lastly, it is an object of the present invention to provide a new and improved syringe storage device for safely securing a syringe during ambulance treatment and transport of patients.

These together with other objects of the invention, along with the various features of novelty that characterize the invention, are pointed out with particularity in the claims annexed to and forming a part of this disclosure. For a better understanding of the invention, its operating advantages, and the specific objects attained by its uses, reference should be had to the accompanying drawings and descriptive matter in which there is illustrated current embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DESCRIPTION OF THE CURRENT EMBODIMENT

Figure 1:
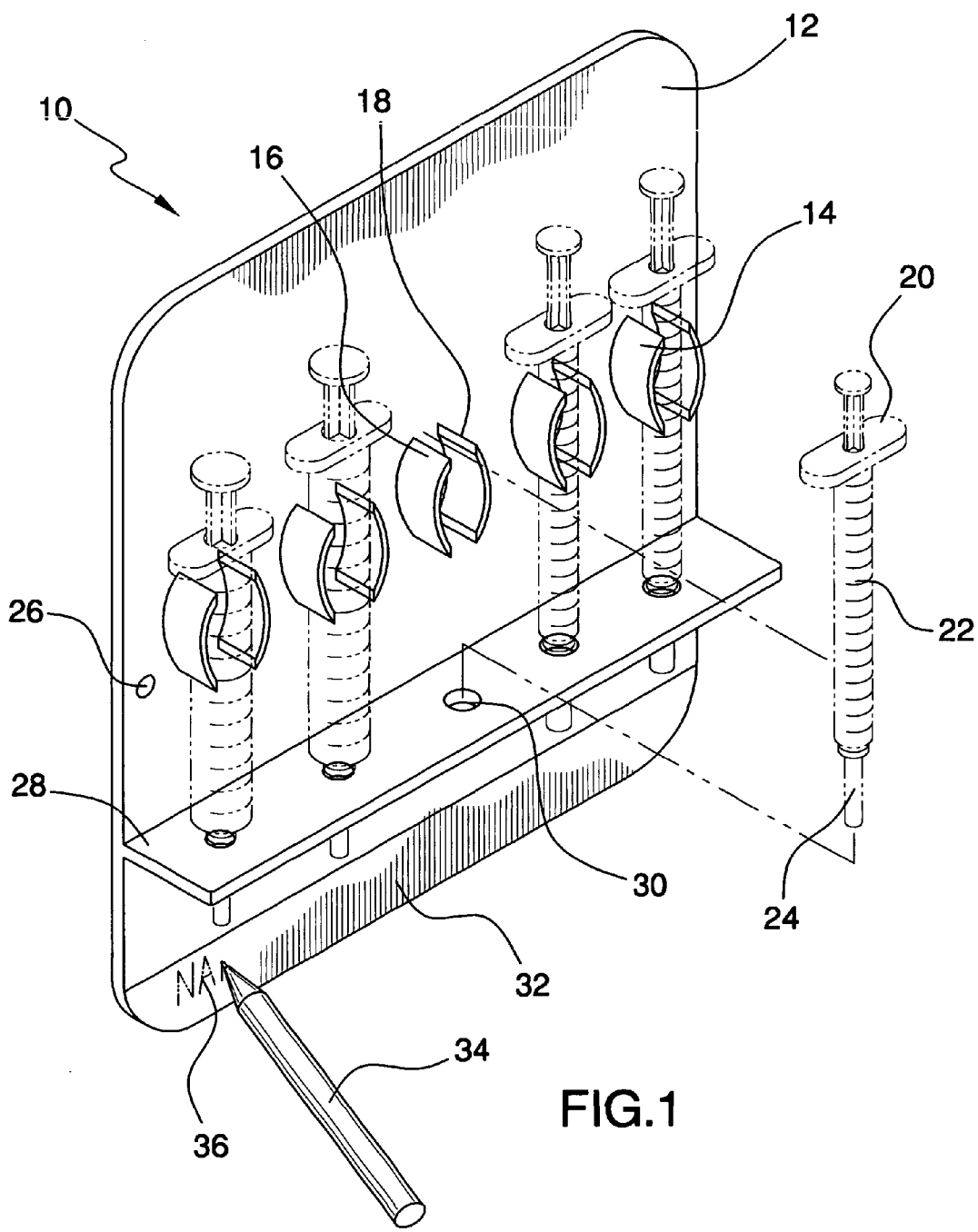
FIG. 1. is a top perspective view of the current embodiment of the syringe storage device constructed in accordance with the principles of the present invention.

Referring now to the drawings, and particularly to FIGS. 1–4, a current embodiment of the syringe storage device of the present invention is shown and generally designated by the reference numeral 10.

In FIG. 1, a new and improved syringe storage device 10 of the present invention for safely securing a syringe during ambulance treatment and transport of patients is illustrated and will be described. More particularly, the syringe storage device 10 has a base 12 with a plurality of clips 14 and one side of a shelf 28 attached to its front. Each clip 14 has a left clip member 16 and a right clip member 18 which are arctuate in shape, mirror images of each other, and adapted to fit a syringe body 22. A plurality of needle holes 30 are present in the middle of the shelf 28 centered beneath the clips 14. The needle holes 30 are adapted to receive a needle cover 24. The bottom of the front of the base 12 comprises a dry erase board 32 to which a syringe label 36 can be removably affixed by a user writing with a dry erase pen 34. A syringe 20 is easily removably secured to the base 12 by inserting its needle cover 24 into an appropriately sized needle hole 30 and snapping its syringe body 22 into a corresponding appropriately sized clip 14. The contents of the syringe 20 can be written on the dry erase board 32 portion of the base 12 beneath it to facilitate identification. A plurality of mounting holes 26 are present in the opposing sides of the base 12 to facilitate the attachment of the base 12 to an interior wall or cabinet in an ambulance. In the current embodiment, the base 12 is made of molded plastic, is washable, is generally square in shape with rounded corners, and has a length of six inches and a height of six inches. The clips 14 are made of molded plastic and a plurality of the clips 14 and corresponding needle holes 30 accommodate a 1 cc syringe in the current embodiment. Note that the dry erase pen 34 and the broken lines illustrating syringe label 36 and syringes 20 with syringe bodies 22 and needle covers 24 are for illustrative purposes only and are not part of the current embodiment.

Figure 2:
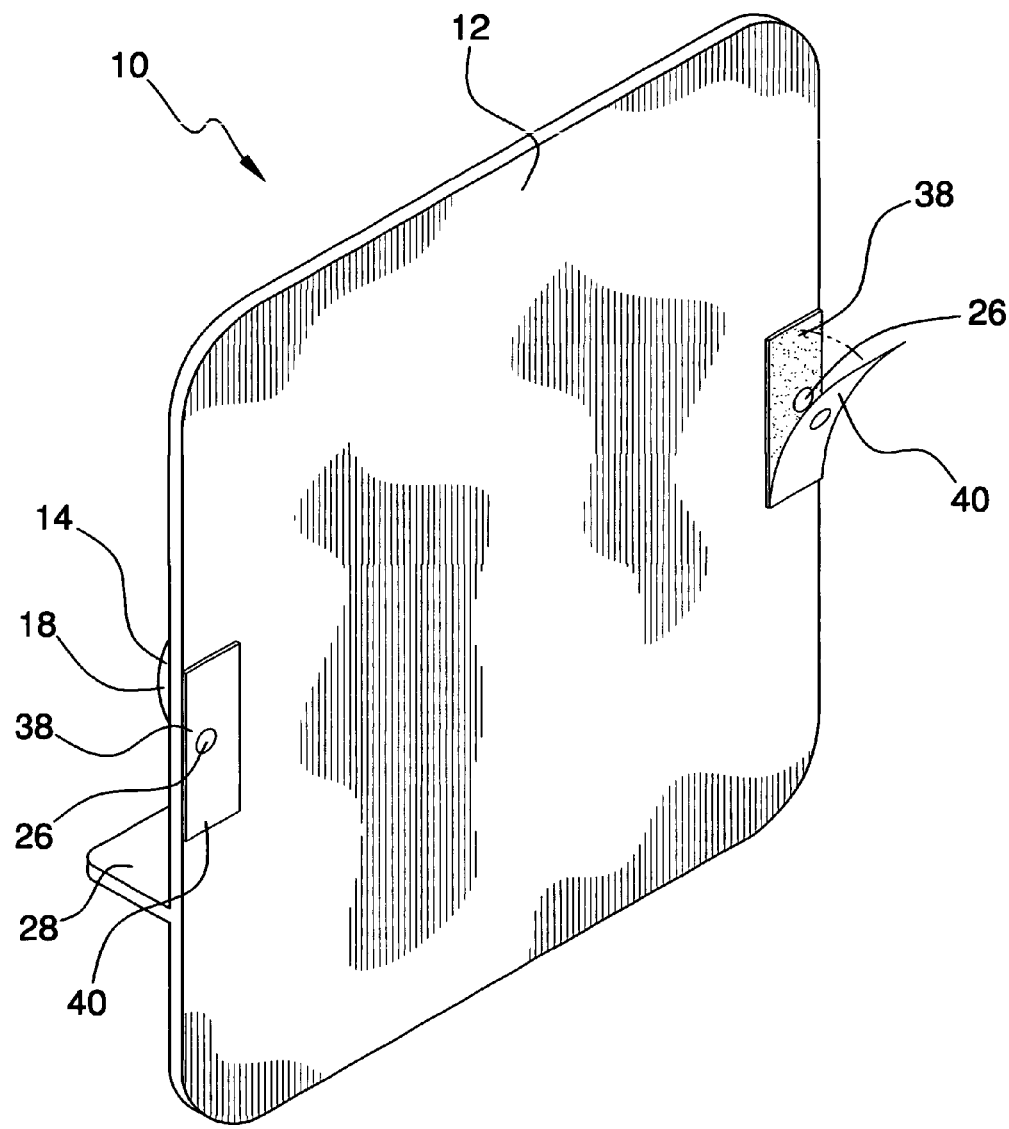
FIG. 2 is a top perspective view of the syringe storage device of the present invention.

Moving on to FIG. 2, a new and improved syringe storage device 10 of the present invention for safely securing a syringe during ambulance treatment and transport of patients is illustrated and will be described. More particularly, the syringe storage device 10 has a plurality of adhesive tabs 38 with their fronts attached to the back of the base 12. The adhesive tabs 38 are positioned over the mounting holes 26 present in the base 12. Corresponding mounting holes 26 are present in the middle of the adhesive tabs 38 and, optionally, in the middle of the peel off backings 40. The peel off backings 40 removably cover the adhesive tabs 38 to keep them free from contamination. The peel off backings 40 can be removed from the adhesive tabs 38 to allow the adhesive tabs 38 to attach the base 12 to an interior wall or cabinet in an ambulance. A portion of the right clip member 18 of clip 14 and shelf 28 are also visible.

Figure 3:
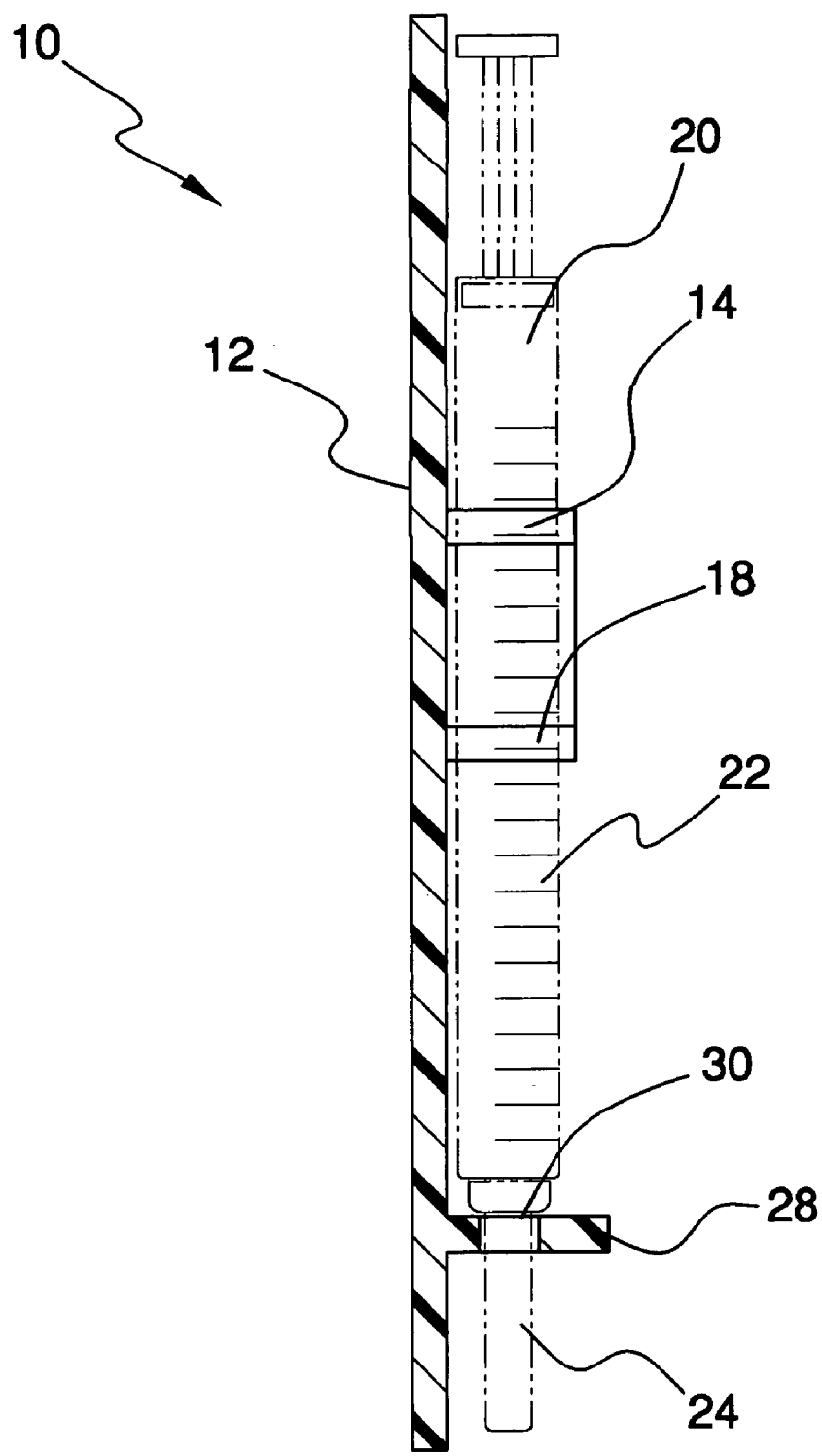
FIG. 3 is a left side sectional view of the syringe storage device of the present invention.

Continuing with FIG. 3, a new and improved syringe storage device 10 of the present invention for safely securing a syringe during ambulance treatment and transport of patients is illustrated and will be described. More particularly, the syringe storage device 10 has a base 12 with the right clip member 18 of a clip 14 attached to its front. A shelf 28 with a needle hole 30 in its middle is attached to one side of the front of the base 12. A syringe 20 is shown removably secured in the syringe storage device 10 with its needle cover 24 removably inserted through needle hole 30 and its syringe body 22 removably secured by clip 14. Note that the broken lines illustrating syringe 20 with syringe body 22 and needle cover 24 are for illustrative purposes only and are not part of the current invention.

Figure 4:
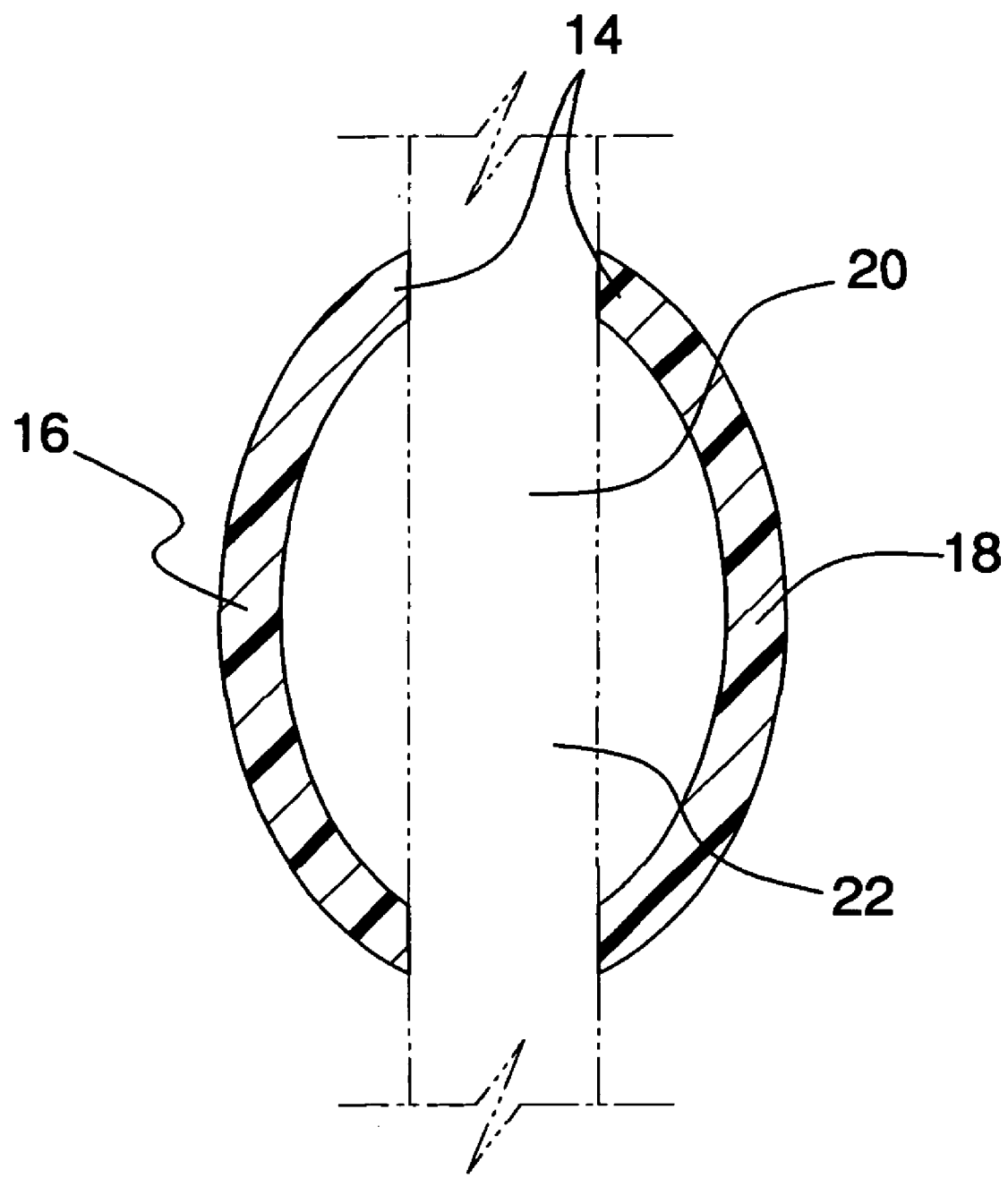
FIG. 4 is a front side sectional view of the clip of the present invention.

Concluding with FIG. 4, a new and improved clip 14 of the present invention for safely securing a syringe during ambulance treatment and transport of patients is illustrated and will be described. More particularly, the clip 14 has a left clip member 16 and a right clip member 18 which are adapted to removably secure the syringe body 22 of a syringe 20. Note that the broken lines illustrating the syringe 20 with syringe body 22 are for illustrative purposes only and are not part of the current invention.

In use, it can now be understood that the user can either remove the peel off backings 40 to attach the adhesive tabs 38 to an interior wall or cabinet of an ambulance, insert screws or nails through mounting holes 26 to attach the syringe storage device 10 to an interior wall or cabinet of an ambulance, or use both the adhesive tabs 38 and screws or nails to attach the syringe storage device 10 to an interior wall or cabinet of an ambulance. As needed, the user removably secures a syringe 20 to the syringe storage device 10 by inserting its needle cover 24 into an appropriately sized needle hole 30 and snapping its syringe body 22 into the corresponding appropriately sized clip 14 located directly above the needle hole 30. The user can use a dry erase pen 34 to write a syringe label 36 on the dry erase board 32 portion of the base 12 to label the contents of the syringe 20. To access the syringe 20, the user pulls syringe body 22 out of clip 14 and then lifts needle cover 24 out of the needle hole 30. When the syringe label 36 no longer accurately reflects the contents of the syringe 20 stored above it, the user can wipe off the syringe label 36 and write a new one using dry erase pen 34.

While a current embodiment of the syringe storage device has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. For example, any suitable sturdy material such as steel, aluminum, titanium, wood, or carbon fiber composite may be used instead of the plastic base described. Also, the plastic clip may also be made of steel, aluminum, titanium, wood, or carbon fiber composite. And although safely securing a syringe during ambulance treatment and transport of patients has been described, it should be appreciated that the syringe storage device herein described is also suitable for being installed in a wide variety of locations. Furthermore, a wide variety of other cylindrical-shaped objects, such as pens and pencils, may be used instead of the syringes described.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A syringe storage device comprising:
   a base having a front, a back, opposing sides, and opposing ends wherein at least a portion of said front of said base comprises a dry erase board;
   a plurality of left clip members attached to said front of said base;
   a plurality of right clip members attached to said front of said base;
   a shelf having opposing sides and a middle with one of said opposing sides attached to one of said opposing ends of said front of said base;
   a plurality of needle holes wherein said middle of said shelf defines holes therein to comprise said needle holes;
   a plurality of mounting holes wherein said opposing sides of said base define a hole therein to comprise said mounting holes;
   a plurality of adhesive tabs having a front, a back, and a middle with said front attached to said back of said base atop said mounting holes;
   a plurality of peel off backings removably attached to said back of said adhesive tabs; and
   a plurality of mounting holes wherein said middle of said adhesive tabs defines a hole therein to comprise said mounting holes.

2. The syringe storage device as defined in claim 1, wherein a plurality of said left clip members, said right clip members, and said needle holes are adapted to hold a 1 cc syringe.

\* \* \* \* \*